US012740732B2

(12) United States Patent
Kang et al.

(10) Patent No.: US 12,740,732 B2
(45) Date of Patent: Sep. 22, 2026

(54) BODY-INSERTION DEVICE AND METHOD FOR CONTROLLING THE SAME

(71) Applicant: AIRS MEDICAL CO., LTD., Seoul (KR)

(72) Inventors: Seung Man Kang, Seoul (KR); Hyung Rok Kim, Seoul (KR); Hye Seong Lee, Seoul (KR); Yun Myeong Kim, Seoul (KR)

(73) Assignee: AIRS MEDICAL CO., LTD., Seoul (KR)

(*) Notice: Subject to any disclaimer, the term of this patent is extended or adjusted under 35 U.S.C. 154(b) by 947 days.

(21) Appl. No.: 17/960,526

(22) Filed: Oct. 5, 2022

(65) Prior Publication Data

US 2023/0024178 A1 Jan. 26, 2023

Related U.S. Application Data

(63) Continuation of application No. PCT/KR2020/016088, filed on Nov. 16, 2020.

(30) Foreign Application Priority Data

Sep. 24, 2020 (KR) ........................ 10-2020-0123787

(51) Int. Cl.
*A61B 5/15* (2006.01)

(52) U.S. Cl.
CPC .... *A61B 5/150175* (2013.01); *A61B 5/15003* (2013.01); *A61B 5/150503* (2013.01); *A61B 5/150732* (2013.01)

(58) Field of Classification Search
CPC .......... A61B 5/150175; A61B 5/15003; A61B 5/150503; A61B 5/150732; A61B 5/150748; A61B 5/1535; A61B 5/3287; A61B 5/427; A61B 5/489; A61B 5/46; A61B 5/1545; A61B 8/0841; A61B 8/469; A61B 8/5223; A61B 8/085; A61B 34/30;

(Continued)

(56) References Cited

U.S. PATENT DOCUMENTS 4,297,725 A 10/1981 Shimizu et al.
6,665,554 B1 12/2003 Charles et al.

(Continued)

FOREIGN PATENT DOCUMENTS

CN 1501727 A 6/2004
CN 1709205 A 12/2005

(Continued)

OTHER PUBLICATIONS

Zhi Wang et al., "Mobile Positioning in Blind Environments (I): Pattern Recognition Algorithms for Coded Sequence Pattern Signposts", Journal of Northeastern University (Natural Science), vol. 32, No. 5, May 2011.

*Primary Examiner* — Jennifer Robertson
*Assistant Examiner* — Nidhi N Patel
(74) *Attorney, Agent, or Firm* — McDonald Hopkins LLC

(57) ABSTRACT

A body-insertion device for a body includes an adjustment unit for adjusting bevel orientation of a needle, and a moving unit for the needle. The moving unit supports a needle unit having the needle, the bevel orientation of which is adjusted by the adjustment unit; adjusts the needle unit to the orientation which is appropriate for body-insertion; and moves the needle unit for body-insertion.

16 Claims, 15 Drawing Sheets

(58) Field of Classification Search
CPC ............ A61B 34/20; A61B 2017/3413; A61B 2017/3409; A61B 2034/2055; A61B 2034/2059; A61B 2034/2063; A61B 2034/2065; A61B 2090/065
See application file for complete search history.

(56) References Cited

U.S. PATENT DOCUMENTS

| | | | |
|---|---|---|---|
| 7,621,933 | B2 | 11/2009 | Bodduluri et al. |
| 7,621,934 | B2 | 11/2009 | Bodduluri et al. |
| 7,806,121 | B2 | 10/2010 | Bodduluri |
| 7,962,192 | B2 | 6/2011 | Bodduluri et al. |
| 8,104,480 | B2 | 1/2012 | Bodduluri |
| 8,133,247 | B2 | 3/2012 | Bodduluri et al. |
| 8,690,894 | B2 | 4/2014 | Bodduluri et al. |
| 9,333,307 | B2 | 5/2016 | Schwaiger et al. |
| 9,526,581 | B2 | 12/2016 | Bodduluri et al. |
| 10,299,871 | B2 | 5/2019 | Zingaretti et al. |
| 10,327,850 | B2 | 6/2019 | Bodduluri et al. |
| 2007/0016067 | A1 | 1/2007 | Webster, III et al. |
| 2007/0078466 | A1 | 4/2007 | Bodduluri et al. |
| 2007/0078473 | A1 | 4/2007 | Bodduluri et al. |
| 2007/0078475 | A1 | 4/2007 | Bodduluri et al. |
| 2007/0106306 | A1 | 5/2007 | Bodduluri et al. |
| 2007/0106307 | A1 | 5/2007 | Bodduluri et al. |
| 2007/0150247 | A1 | 6/2007 | Bodduluri |
| 2008/0167674 | A1 | 7/2008 | Bodduluri et al. |
| 2008/0221519 | A1 | 9/2008 | Schwach et al. |
| 2009/0275823 | A1 | 11/2009 | Ayati et al. |
| 2010/0030234 | A1 | 2/2010 | Bodduluri et al. |
| 2010/0063515 | A1 | 3/2010 | Fisher et al. |
| 2010/0278785 | A1 | 11/2010 | Schwaiger et al. |
| 2011/0022371 | A1 | 1/2011 | Bodduluri |
| 2011/0224693 | A1 | 9/2011 | Bodduluri et al. |
| 2012/0190981 | A1 | 7/2012 | Harris et al. |
| 2013/0131502 | A1 | 5/2013 | Blaivas et al. |
| 2014/0155912 | A1 | 6/2014 | Bodduluri et al. |
| 2014/0276062 | A1 | 9/2014 | Kondoh |
| 2016/0324586 | A1 | 11/2016 | Zingaretti et al. |
| 2017/0056114 | A1 | 3/2017 | Bodduluri et al. |
| 2018/0150598 | A1* | 5/2018 | Kohls .................... G16H 50/20 |

FOREIGN PATENT DOCUMENTS

| | | | |
|---|---|---|---|
| CN | 108814691 | A | 11/2018 |
| CN | 109602499 | A | 4/2019 |
| CN | 111134727 | A | 5/2020 |
| JP | 2008-113904 | A | 5/2008 |
| JP | 2008-522705 | A | 7/2008 |
| JP | 2008-545502 | A | 12/2008 |
| JP | 2010-201049 | A | 9/2010 |
| JP | 2013-039246 | A | 2/2013 |
| JP | 2015-501686 | A | 1/2015 |
| KR | 10-2010-0057792 | A | 6/2010 |
| KR | 10-2010-0117708 | A | 11/2010 |
| KR | 10-1601421 | B1 | 3/2016 |
| KR | 10-1615036 | B1 | 4/2016 |
| KR | 1016150360000 | B1 | 4/2016 |
| KR | 10-2018-0012510 | A | 2/2018 |
| KR | 10-2246966 | B1 | 4/2021 |
| KR | 10-2021-0123238 | A | 10/2021 |
| WO | 2007/041267 | A2 | 4/2007 |
| WO | 2008/043091 | A2 | 4/2008 |
| WO | 2009/013011 | A2 | 1/2009 |
| WO | 2018/017811 | A1 | 1/2018 |
| WO | 2019/235518 | A1 | 12/2019 |
| WO | 2020/076942 | A2 | 4/2020 |
| WO | 2020/142338 | A1 | 7/2020 |

* cited by examiner

BODY-INSERTION DEVICE AND METHOD FOR CONTROLLING THE SAME

CROSS-REFERENCE TO RELATED APPLICATION

This application is a Continuation of International Application No. PCT/KR2020/016088, filed on Nov. 16, 2020, which claims priority to Korean Application No. 10-2020-0123787, filed on Sep. 24, 2020. Both applications are incorporated herein by reference in their entireties.

TECHNICAL FIELD

The present disclosure relates to a body-insertion device and a method for controlling the device. Specifically, the present disclosure relates to a device which adjusts a bevel orientation of a venipuncture needle or blood collection needle to be inserted into a body and a method for controlling the device.

RELATED ART

In hospitals or clinics, a medical procedure that a medical instrument is inserted into a body are frequently performed for various purposes. For example, a venipuncture needle is inserted into a superficial vein for blood collection or intravenous injection and a catheter is inserted into some organs. In this specification, a venipuncture needle or blood collection needle is simply referred to as "needle" for brevity. Currently, a medical doctor, a nurse or a pathologist who is trained to find the insertion location of blood vessel such as a superficial vein performs the insertion. The current system needs a long time for training the medical staffs and labor costs are incurred. Further, if a needle is not inserted at an appropriate location, the medical staff additionally tries to insert the needle into the body and a person whom the needle is inserted may experience unnecessary pain due to the additional needle insertion. Even a specialist has difficulties when inserting a needle into a person with poor blood vessel conditions such as a baby, an old person, a patient undergoing chemotherapy, a person having dark skin, and the like.

Repeated blood collection work can cause high fatigue and a lot of discomfort even for the experienced medical staffs. Further, a medical staff performing blood collection is exposed to infection risks when blood splashes onto the staff or enters the staff's body during the blood collection procedure.

The applicant filed a Korean Patent Application No. 10-2020-0010302 on Jan. 29, 2020 (KR Patent No. 10-2246966) for a method for exactly detecting a location of a target of a body such as a superficial vein by use of a machine learning. The applicant also filed a Korean Patent Application No. 10-2020-0040097 on Apr. 2, 2020 for a body-insertion device. The applications are incorporated herein in their entireties.

SUMMARY

The object of the present disclosure is to provide a body-insertion device wherein a bevel orientation of a needle can be adjusted and a method for controlling the device In order to accomplish the object, the present disclosure provides a body-insertion device for a body, which comprises an adjustment unit for adjusting bevel orientation of a needle; and a moving unit for the needle. The moving unit supports a needle unit having the needle, the bevel orientation of which is adjusted by the adjustment unit; adjusts the needle unit to the orientation which is appropriate for body-insertion; and moves the needle unit for body-insertion.

The device of the present disclosure can further comprises a transfer unit for moving the needle unit to a second position from a first position.

The adjustment unit can comprise a support arm for supporting the needle unit; a driving module for rotating the support arm; and a detector for detecting the bevel orientation of the needle.

The adjustment unit can comprise at least one roller which is configured to be in contact with the needle unit; a seventh driving module which rotates the roller, thereby rotating the needle unit; and a detector for detecting the bevel orientation of the needle.

The transfer unit can comprise a movable arm which supports the needle unit, the movable arm moving between the first position and the second position.

The adjustment unit can be provided in at least one of the first position or the second position, or close to the positions.

The adjustment unit can further comprise a movement prohibitor which prevents the needle unit from moving in the direction other than the rotation direction caused by the roller.

The device of the present disclosure can further comprise a probe unit for probing a target body, wherein the probe unit comprises a probe, a probe holder, a pressing module for pressing the target body.

The probe unit can further comprise an elastic member for connecting the probe holder and the pressing module.

The roller can comprise teeth portion which is in contact with the outer periphery of the needle unit or meshes with teeth portion of the needle unit.

The computer-implemented method for controlling the device according to the present disclosure comprises a first step of supporting, by the moving unit, the needle unit; a second step of, by the adjustment unit, adjusting the bevel orientation of the needle; a third step of, by the moving unit, adjusting the orientation of the needle unit into the appropriate orientation for body-insertion; and a fourth step of, by the moving unit, performing body-insertion.

The computer-implemented method for controlling the device according to another aspect of the present disclosure comprises a first step of, by the adjustment unit, adjusting the bevel orientation of the needle; a second step of, by the transfer unit, moving the needle unit to the second position from the first position; a third step of, by the moving unit, receiving the needle unit at the second position and supporting the needle unit; a fourth step of, by the moving unit, adjusting the needle unit into the appropriate orientation for body-insertion; and a fifth step of, by the moving unit, moving the needle unit for body-insertion.

The computer-implemented method for controlling the device according to still other aspect of the present disclosure comprises a first step of, by the moving unit, supporting the needle unit; a second step of, by the adjustment unit, adjusting the bevel orientation of the needle; a third step of moving the pressing module on the target body while pressing a body; a fourth step of, by the moving unit, adjusting the orientation of the needle unit into the appropriate orientation for body-insertion; and a fifth step of, by the moving unit, moving the needle unit for body-insertion.

The computer-implemented method for controlling the device according to still other aspect of the present disclosure comprises a first step of, by the adjustment unit, adjusting the bevel orientation of the needle; a second step of, by the transfer unit, moving the needle unit to the second position from the first position; a third step of, by the moving unit, receiving the needle unit at the second position and supporting the needle unit; a fourth step of moving the pressing module on the target body while pressing a body; and a fifth step of, by the moving unit, moving the needle unit for body-insertion.

The pressing module can linearly move on the body.

The pressing module can move on the body over a predetermined distance.

An adjustment device of the present disclosure comprises a support for supporting at least one of the inner side or the outer side of the needle unit; and a driving module for rotating the support to adjust the bevel orientation of the needle.

An adjustment device of another aspect of the present disclosure comprises a support for supporting at least one of the inner side and the outer side of the needle unit; at least one roller which is in contact with the needle unit; and a driving module for rotating the roller to adjust the bevel orientation of the needle.

The roller can comprise teeth portion which is in contact with the outer periphery of the needle unit or meshes therewith.

The driving module can be a rotation driving module or a linear driving module.

According to the present disclosure, the bevel of a needle can be adjusted to have a desired orientation so that the needle can be smoothly inserted into a body. Further, according to the present disclosure, a blood vessel is linearized so that the detection of the blood vessel and the blood collection can be easily achieved.

Figure 1:
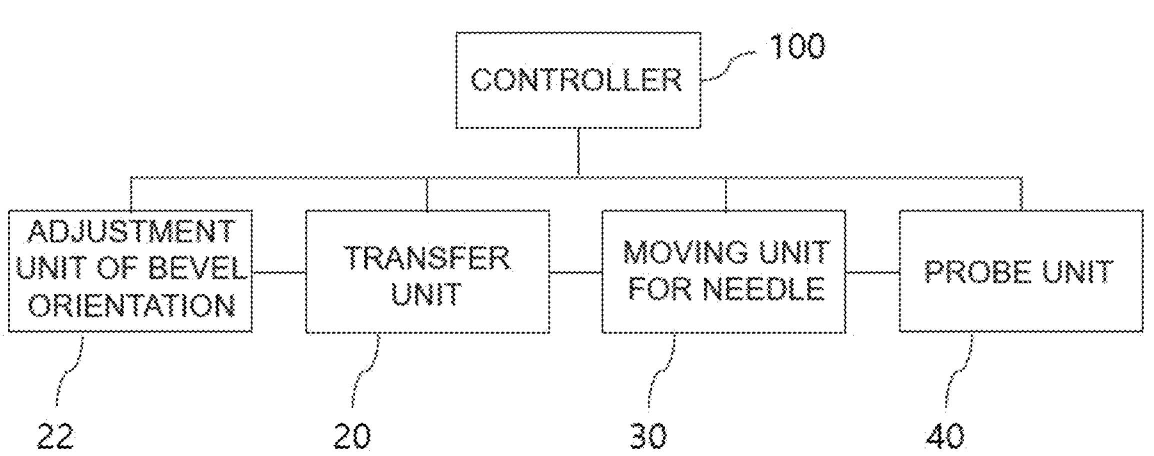
FIG. 1 is a block diagram of the body-insertion device according to the present disclosure.

It should be understood that the above-referenced drawings are not necessarily to scale, presenting a somewhat simplified representation of various preferred features illustrative of the basic principles of the disclosure. The specific design features of the present disclosure will be determined in part by the particular intended application and use environment.

DETAILED DESCRIPTION

Hereinafter, the present disclosure will be described in detail with reference to the accompanying drawings. As those skilled in the art would realize, the described embodiments may be modified in various different ways, all without departing from the spirit or scope of the present disclosure. Further, throughout the specification, like reference numerals refer to like elements.

In this specification, the order of each step should be understood in a non-limited manner unless a preceding step must be performed logically and temporally before a following step. That is, except for the exceptional cases as described above, although a process described as a following step is preceded by a process described as a preceding step, it does not affect the nature of the present disclosure, and the scope of rights should be defined regardless of the order of the steps. In addition, in this specification, "A or B" is defined not only as selectively referring to either A or B, but also as including both A and B. In addition, in this specification, the term "comprise" has a meaning of further including other components in addition to the components listed.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. The term "coupled," "connected," or "fastened" denotes a physical relationship between two components whereby the components are either directly connected to one another or indirectly connected via one or more intermediary components.

The terms "first," "second," or the like are herein used to distinguishably refer to same or similar elements, or the steps of the present disclosure and they may not infer an order or a plurality.

In this specification, the essential elements for the present disclosure will be described and the non-essential elements may not be described. However, the scope of the present disclosure should not be limited to the invention including only the described components. Further, it should be understood that the invention which includes additional element or does not have non-essential elements can be within the scope of the present disclosure.

The control method of the present disclosure can be carried out by an electronic arithmetic device.

The electronic arithmetic device can be a device such as a computer, tablet, mobile phone, portable computing device, stationary computing device, server computer etc. Additionally, it is understood that one or more various methods, or aspects thereof, may be executed by at least one processor. The processor may be implemented on a computer, tablet, mobile device, portable computing device, etc. A memory configured to store program instructions may also be implemented in the device(s), in which case the processor is specifically programmed to execute the stored program instructions to perform one or more processes, which are described further below. Moreover, it is understood that the below information, methods, etc. may be executed by a computer, tablet, mobile device, portable computing device, etc. including the processor, in conjunction with one or more additional components, as described in detail below. Furthermore, control logic may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The components of the device can any shape, size, or dimension as well as those which are clearly illustrated in the appended drawings if they can perform the intended functions of the present disclosure. Further, the number of the components of the present disclosure can be differently selected as needed in the extent that it makes the device operable.

FIG. 1 is a block diagram of the body-insertion device according to the present disclosure. As illustrated in FIG. 1, the body-insertion device comprises a controller (100), an adjustment unit of bevel orientation (22), a transfer unit (20), a moving unit for a needle (30), and a probe unit (40).

The controller (100) controls the adjustment unit of bevel orientation (22), the transfer unit (20), the moving unit for needle (30), and the probe unit (40). The controller (100) can be a part of an electronic arithmetic device and can be a logical combination of a universal hardware and software which is conceived to perform particular functions. The control commands of the controller (100) can be generated by computer programs stored in a computer-readable recording media.

Figure 2:
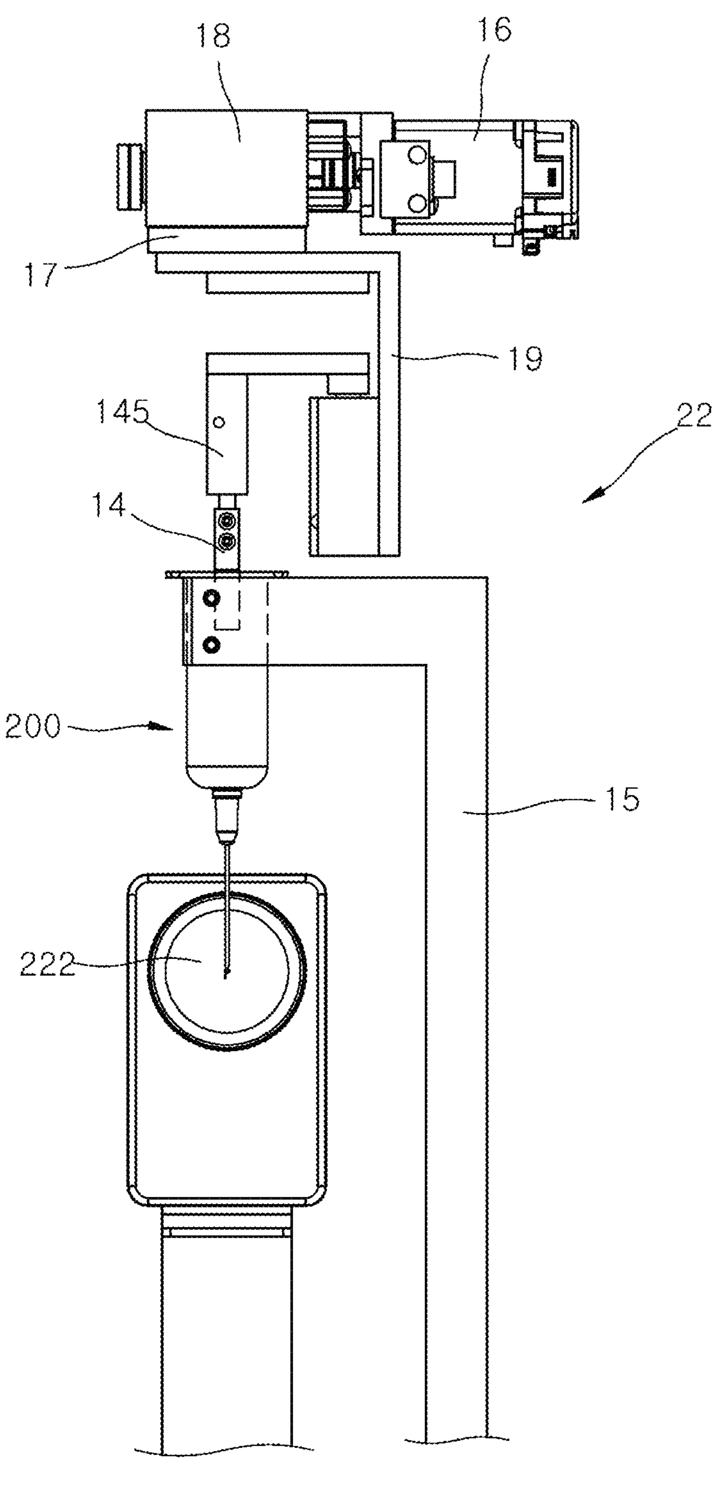
FIG. 2 is a front view of the adjustment unit of the body-insertion device according to the present disclosure.
Figure 3:
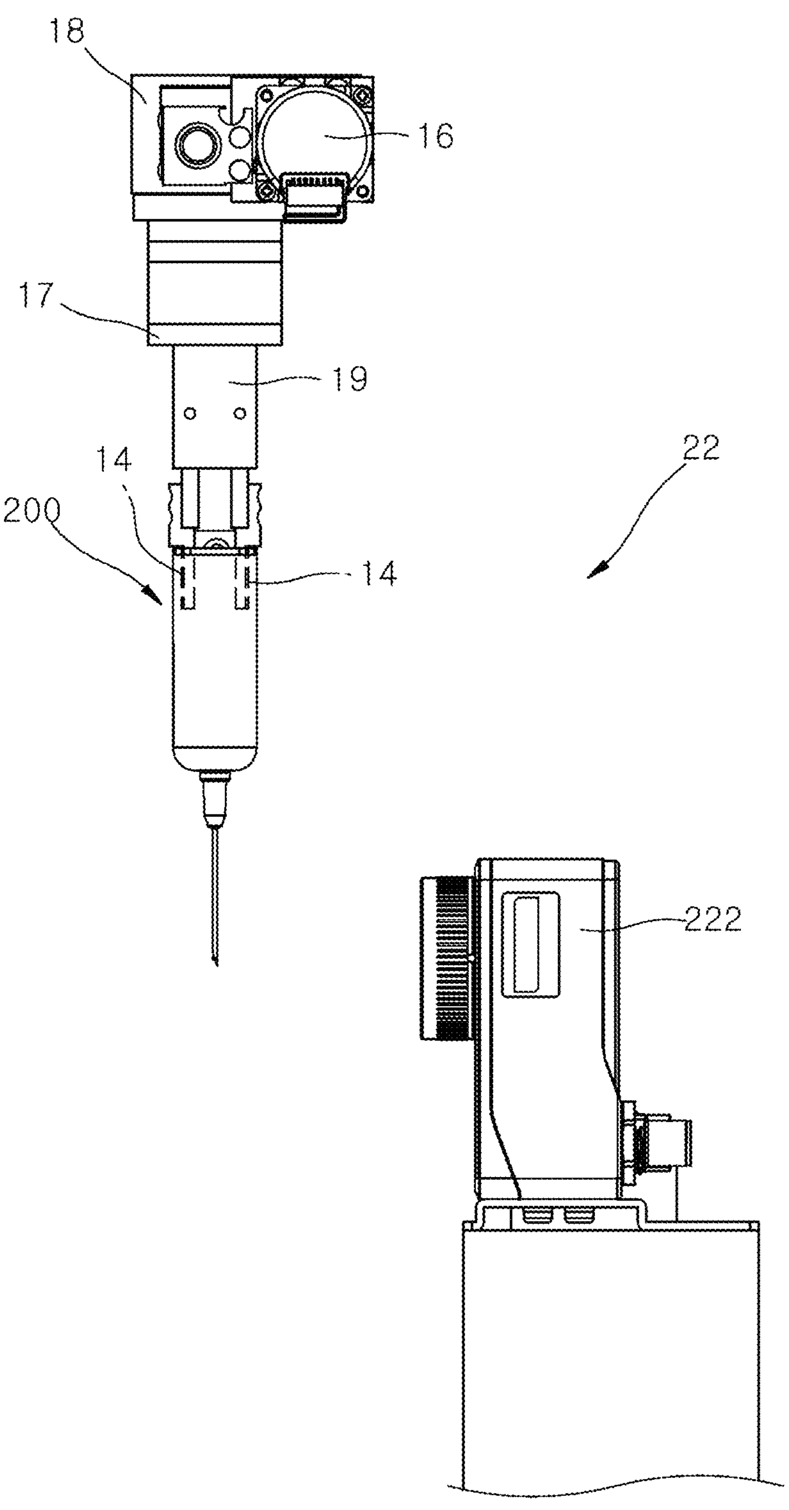
FIG. 3 is a side view of the adjustment unit of the body-insertion device according to the present disclosure.

FIG. 2 is a front view of the adjustment unit of bevel orientation (22), and FIG. 3 is a side view thereof.

The adjustment unit of bevel orientation (22) comprises a first driving module (16), a first direction-change module (18), a first rotation axis (17), a body (19), a second hydraulic module (145), a support arm (14), a support post (15), and a detector (222; for example, a vision sensor). The first rotation axis (17) can be parallel to the lengthwise direction of the needle unit. The support arm (14) can be at least a pair of arms which are parallelly provided to each other and can be driven by the second hydraulic module (145) so that they move toward each other or away from each other. The support arm (14) can be driven to move away from each other so that radial force is outwardly applied to the inner walls of the needle unit (200), thereby supporting the needle unit (200). The bevel orientation of the needle provided at the needle unit (200) can be detected by the detector (222).

If the bevel orientation of the needle of the needle unit (200) is not a desired one, the first driving module (16) rotates the body (19) about the first rotation axis (17) in accordance with the command from the controller (100), thereby adjusting the bevel orientation of the needle of the needle unit (200) supported by the support arm (14) to the desired orientation. The first direction-change module (18) changes the driving force of the first driving module (16) into the force that can rotate the body (19) about the first rotation axis (17). The first direction-change module (18) can include a reducer and can be implemented by use of various known kinematical mechanisms. The change-direction modules to be described in below can also include a reducer. The first driving module (16) can be a rotation driving device for example, a conventional motor or a linear driving device for example, a linear motor. In the event that a linear motor is used, the first direction-change module (18) converts the linear motion into the direction which can rotate the support arm (14).

However, the direction-change module as well as the adjustment unit for bevel orientation are not essential to the present disclosure and can be removed depending on the design of the driving module.

Figure 4:
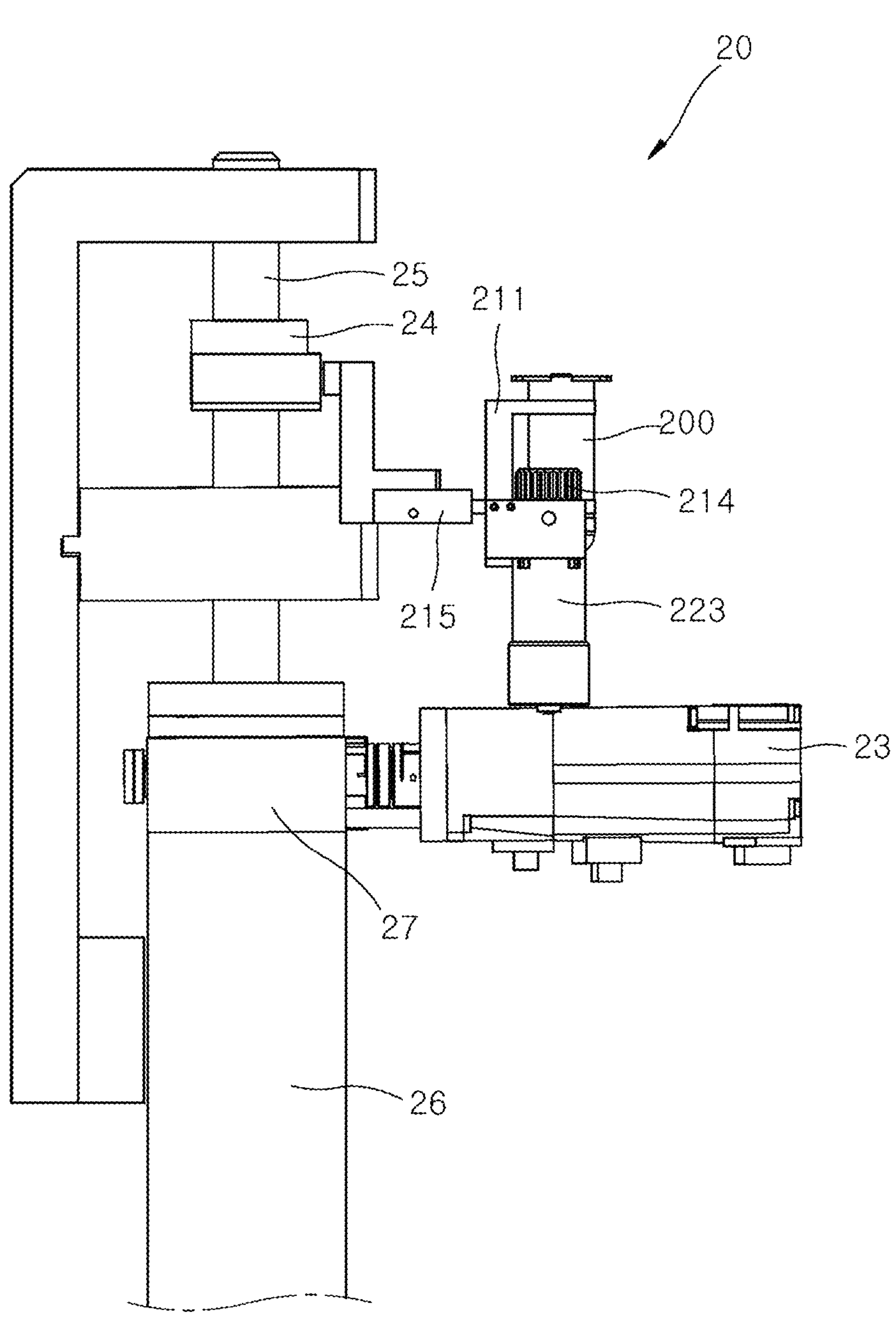
FIG. 4 is a side view of the transfer unit of the body-insertion device according to the present disclosure.
Figure 5:
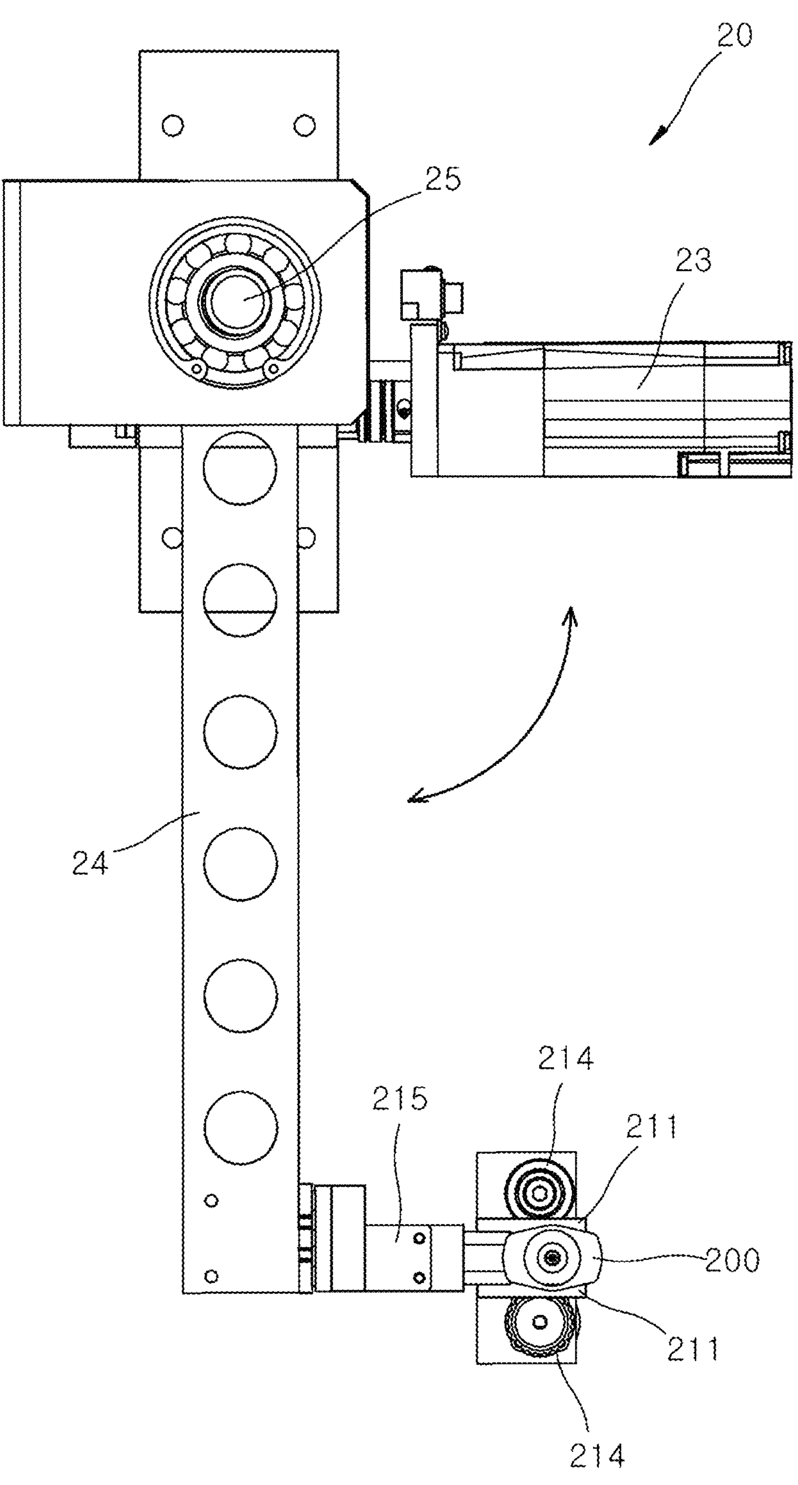
FIG. 5 is a plan view of the transfer unit of the body-insertion device according to the present disclosure.

FIGS. 4 and 5 are a side view and a plan view of the transfer unit (20), respectively. The transfer unit (20) illustrated in FIGS. 4 and 5 can be provided with an adjustment unit of bevel orientation according to another embodiments of the present disclosure. The plan view of the adjustment unit of bevel orientation is illustrated in FIG. 6.

The transfer unit (20) comprises a second driving module (23), a movable arm (24), a second rotation axis (25), a first main body (26), and a second direction-change module (27). The movable arm (24) can be provided with the adjustment unit of bevel orientation according to another embodiments of the present disclosure. The adjustment unit of bevel orientation can comprise at least one roller (214) which is in contact with the needle unit (200), a seventh driving module (223) for rotating the roller (214) to rotate the needle unit (200), and a detector (222; not illustrated in FIGS. 4 to 6). The periphery of the needle unit (200) is supported by the first holder (211) to be maintained at a predetermined position. The first holder (211) can include at least a pair of arms which are parallelly spaced to each other and are driven by a third hydraulic module (215) to move toward each other or away from each other. The arms move toward each other to comes in contact with the outer periphery of the needle unit so as to apply a force toward the needle unit (200), thereby holding the needle unit. The holder (211) can support the needle unit (200) in its inner side as the support arm (14).

The outer periphery of the roller (214) can be provided with teeth portion to be in contact with the outer periphery of the needle unit (200). The needle unit (200) can be provided with complimentary teeth portion in its outer periphery, which can mesh with the teeth portion of the roller. The roller (214) can be made of silicon, synthetic resin, metal and the like.

Figure 6:
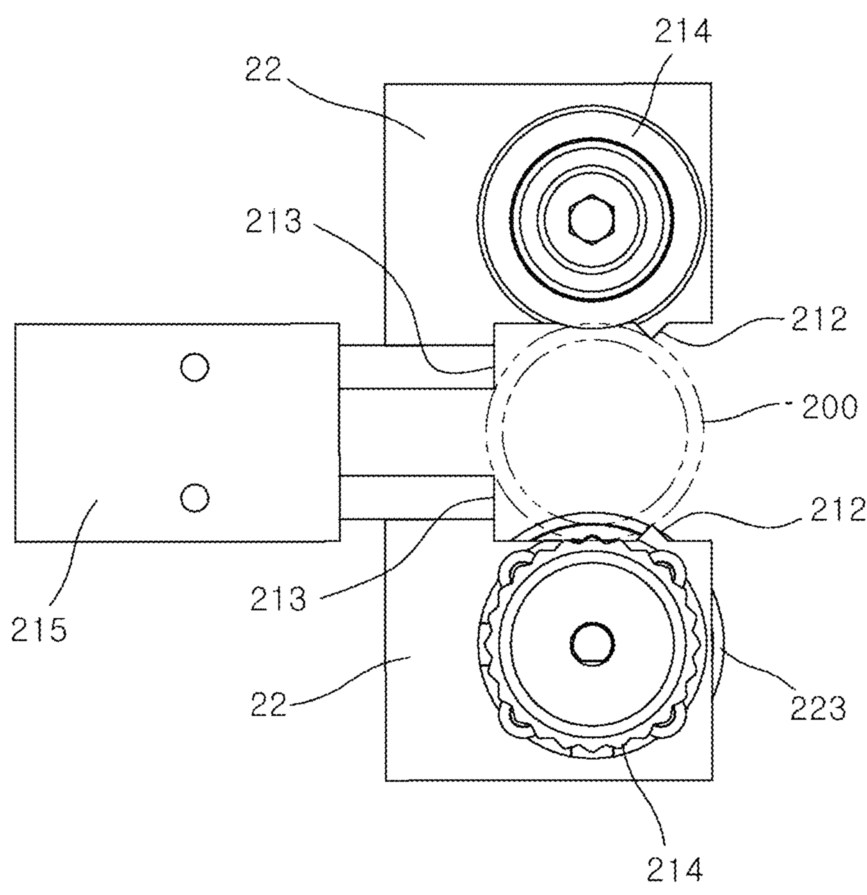
FIG. 6 is a plan view of the adjustment unit according to another embodiments of the present disclosure.

The adjustment unit of bevel orientation illustrated in FIG. 6 can further include a movement prohibitor (212, 213) which can prevent the needle unit (200) from moving in the direction other than the direction where the needle unit (200)

can move by the rollers (214). A plurality of the movement prohibitors (212, 213) can be provided around the outer periphery of the needle unit (200).

The movable arm (24) can be driven by the second driving module (23) to move between a first position and a second position. In this specification, "first position" refers to the position where the needle unit (200) is supplied to the transfer unit (20), and "second position" refers to the position where the needle unit (200) is transferred to the moving unit for needle (30) from the transfer unit (20). The adjustment unit of bevel orientation (22) can be provided at the first position or the second position, or a close position thereto. Alternatively, the adjustment unit of bevel orientation (22) can be disposed at a third position. In that case, the movable arm (24) moves the needle unit (200) to the third position from the first position; the bevel orientation is adjusted at the third position; and then the needle unit (200) is moved to the second position from the third position. In the embodiments, the movable arm which moves the needle unit (200) to the third position from the first position can be separate from the movable arm which moves the needle unit (200) to the second position from the third position.

The position where the adjustment unit of bevel orientation (22) is provided is not essential to the present disclosure. The adjustment unit of bevel orientation can be provided in plural numbers. If the adjustment unit of bevel orientation is disposed at the second position, the movable arm (24) may be unnecessary.

Figure 7:
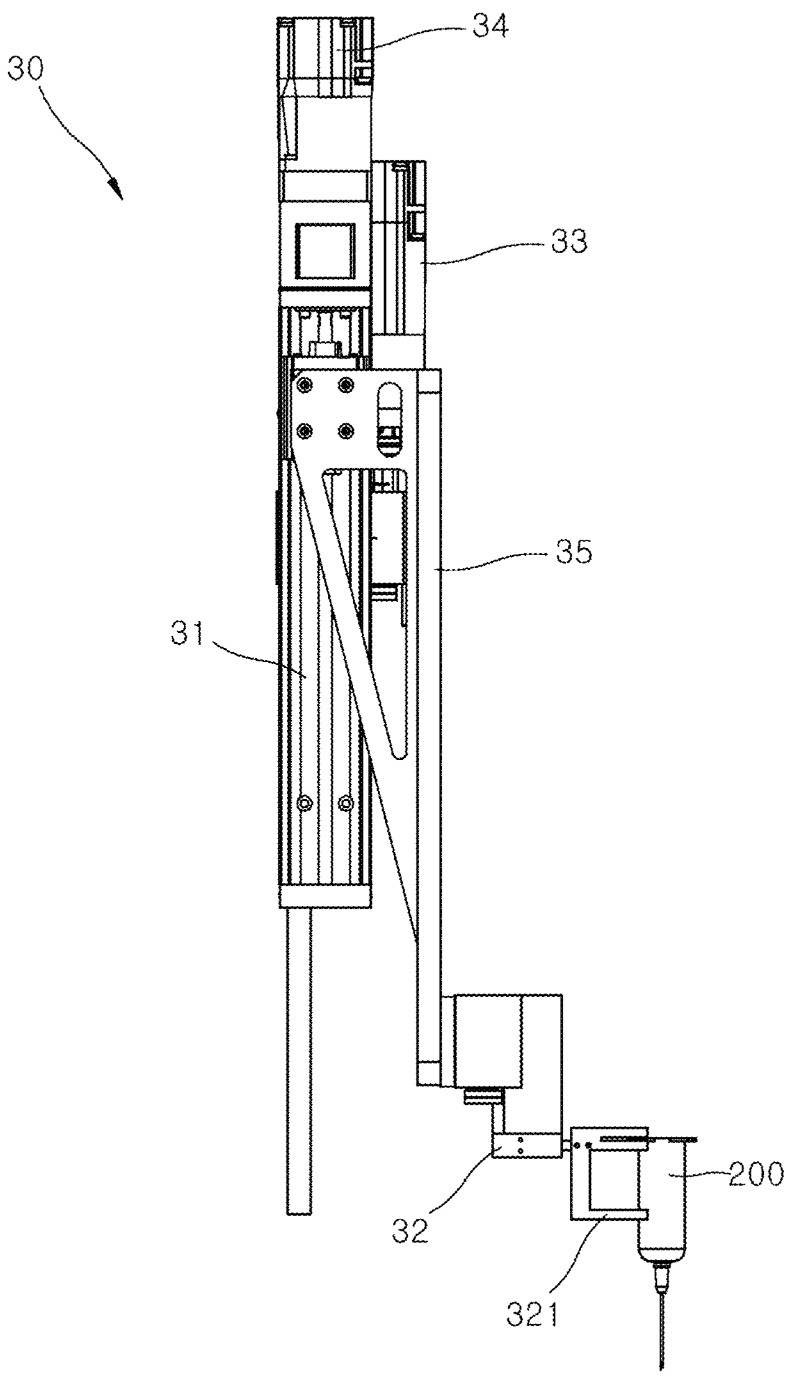
FIG. 7 is a front view of the moving unit for needle of the body-insertion device according to the present disclosure.
Figure 8:
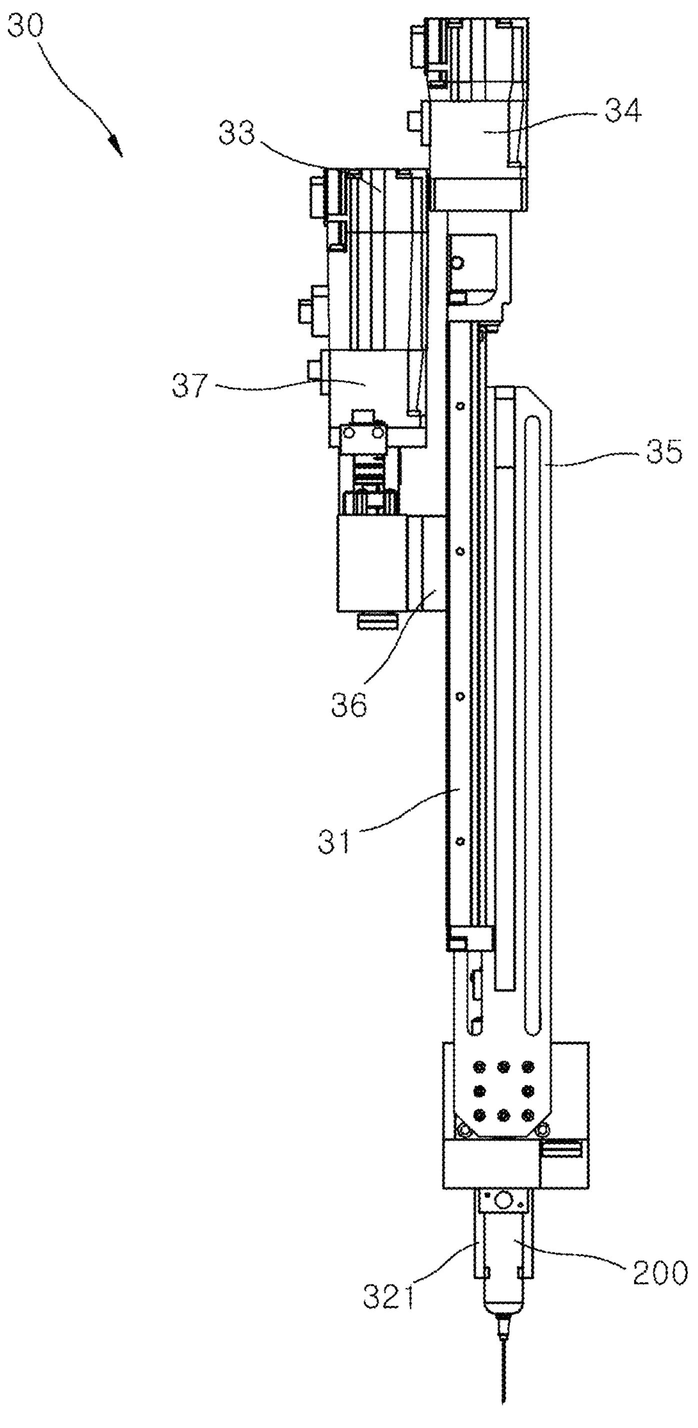
FIG. 8 is a side view of the moving unit for needle of the body-insertion device according to the present disclosure.

FIG. 7 is a front view of the moving unit of needle (30) of the body-insertion device according to the present disclosure and FIG. 8 is a side view thereof.

The moving unit of needle (30) comprises a second main body (31), a first hydraulic module (32), a third driving module (33), a fourth driving module (34), a connecting member (35), a third rotation axis (36) and a third direction-change module (37).

The connecting member (35) supports the needle unit (200) by at least a pair of second holders (321) which are driven by the first hydraulic module (32).

The movable arm (24) moves the needle unit to the second position from the first position, and then the second holder (321) is driven by the first hydraulic module (32) to support the needle unit (200) at the second position. Subsequently, the holding state between the holder (211) and the needle unit (200) is released by the third hydraulic module (215) so that the needle unit (200) is transferred. After the needle unit (200) is transferred, the movable arm (24) returns to the first position.

The connecting member (35) can be provided with an adjustment unit of bevel orientation illustrated in FIGS. 4 to 6. The transfer unit (20) can be unnecessary in the embodiments wherein the needle unit (200) is supplied to the moving unit of needle (30) as illustrated in FIG. 7 and the adjustment unit for bevel orientation is provided in the moving unit of needle (30).

In the state that the needle unit (200) which is transferred to the moving unit of needle (30) is supported by the second holder (321), the needle unit is aligned by the third driving module (33) and the fourth driving module (34) to have the orientation where the needle can be inserted into a body.

First of all, the third driving module (33) rotates the second main body (31) about the third rotation axis (36) to have an angle where the needle can be inserted into the body. The third direction-change module (37) converts the driving force of the third driving module (33) into the rotation force with respect to the third rotation axis (36). In the state that the second main body (31) has the angle by the rotation, the fourth driving module (34) moves the connecting member (35) in the lengthwise direction of the second main body (31) to perform the insertion into the body. The connecting member (35) can move by a ball screw provided along the lengthwise direction of the second main body (31).

The second main body (31) can be provided to further move along at least one of left and right directions of FIGS. 7 and 8, or any other direction although it is not illustrated in the figures.

Figure 9:
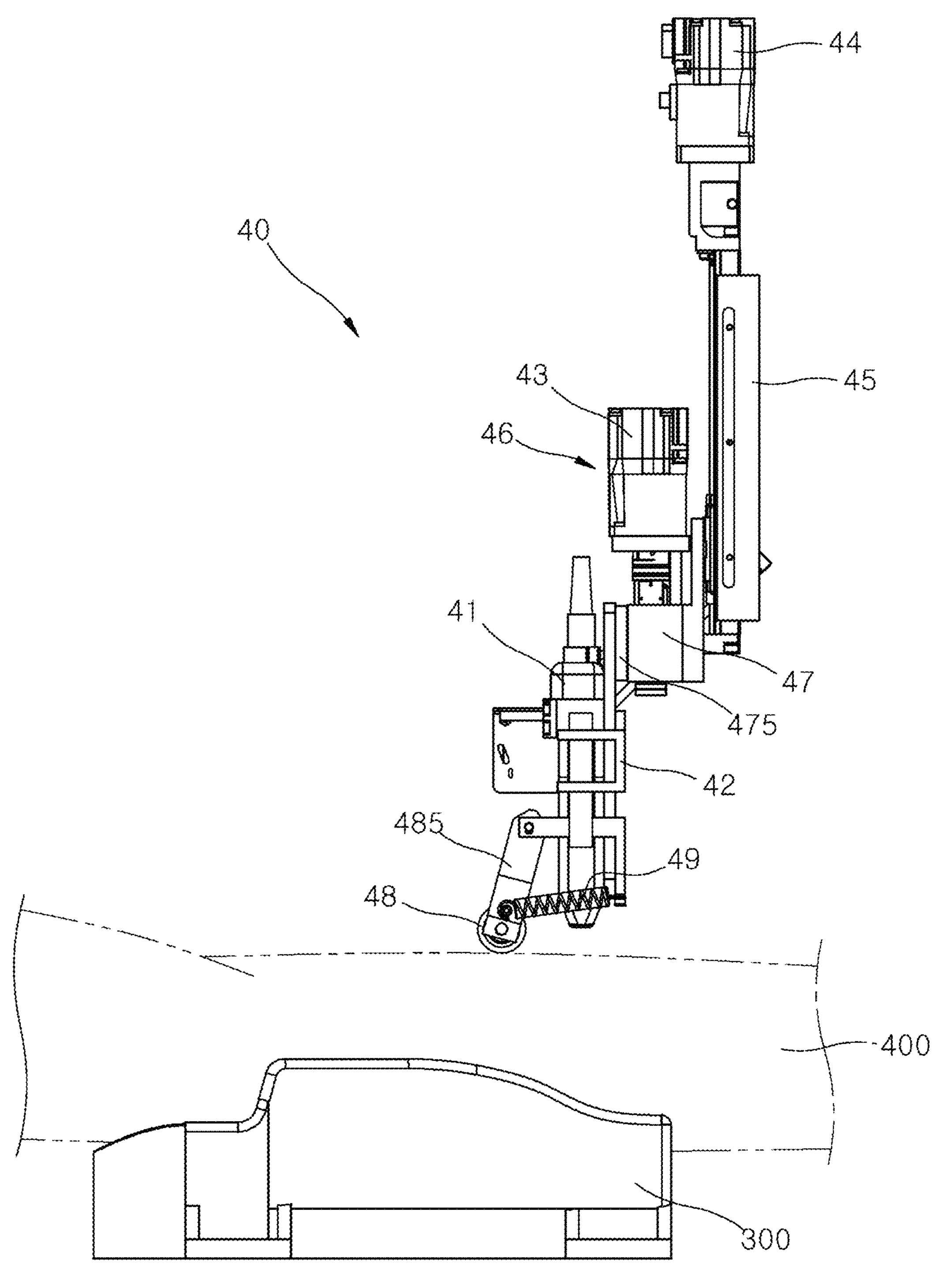
FIG. 9 is a side view of the probe unit of the body-insertion device according to the present disclosure.
Figure 10:
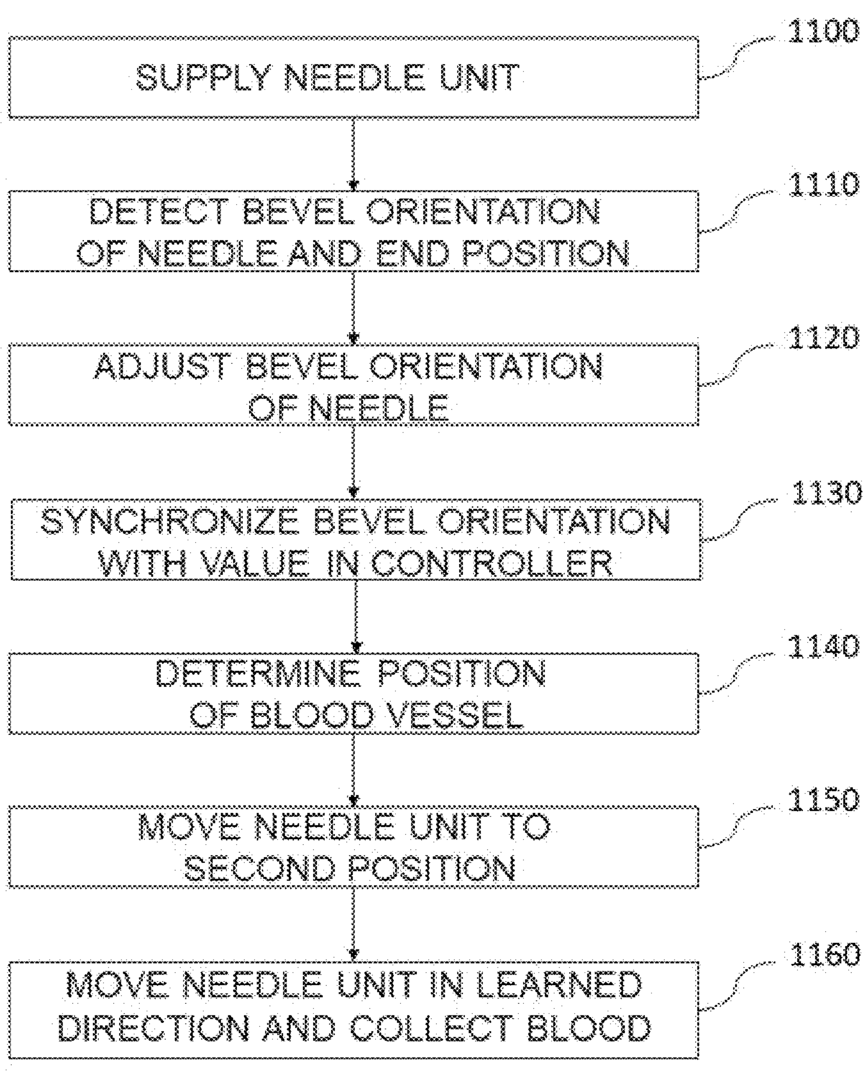
FIG. 10 is a flowchart of the method of body-insertion according to the present disclosure.

FIG. 9 shows a side view of the probe unit (40) according to the present disclosure.

The probe unit (40) of the present disclosure comprises a probe (41), a probe holder (42), a fifth driving module (43), a sixth driving module (44), a rail (45), a moving module (46), a fourth direction-change module (47), a pressing module (48) which is configured to press a target body, and a holder for the pressing module (48). The probe can be an ultrasound probe. The pressing module (48) can be rotatably supported by the holder for the pressing module (48). The pressing module (48) can be a roller. The pressing module (48) and the probe holder (42) are connected to each other via an elastic member (49; for example, spring) so that the pressing module (48) can press the body with a predetermined force.

The probe holder (42) can rotate about the fourth rotation axis (475) by the fifth driving module (43). The fourth direction-change module (47) can convert the driving force of the fifth driving module (43) into the rotation force which rotates the probe holder (42) about the fourth rotation axis (475).

The moving unit (46) can move along the lengthwise direction of the rail (45) by the sixth driving module (44). The rail (45) can be provided with a ball screw.

The probe unit (40) can move in the lengthwise direction of the body (400). The exemplary method for detecting the location of target body (for example, a superficial vein) will be described in below. In the event that the target body is a blood vessel, linearization of the target body can make it easy to detect the location. The linearization can be achieved by moving the probe unit in the lengthwise direction of a body portion (400; for example, a lower arm) while pressing the pressing module (48) to the body portion placed in the body support (300). The pressing module (48) can press the body portion (400) over the distance which is determined to be significant for detection.

Referring to FIGS. 1 to 9, 10 and 11, the operation and control of the device according to the present disclosure are describe in below.

In the step (1100), the needle unit (200) is supplied to, for example, the adjustment unit for bevel orientation (22). As illustrated in FIGS. 2 and 3, the needle unit (200) can be supplied to be supported by the support post (15). Alternatively, the needle unit (200) can be supplied to be supported by the first holder (211) and be disposed between the rollers (214) as illustrated in FIGS. 4 to 6. As described in above, the adjustment unit of bevel orientation can be provided in at least one of the first position and the second position, or adjacent thereto. Alternatively, the adjustment unit of bevel orientation can be provided in a third position or adjacent thereto.

After the needle unit (200) is supplied, the detector (222) recognizes the bevel orientation and the position of the end of the needle in the step (1110). If the bevel orientation is different from the predetermined orientation, the first driving module (16) or the seventh driving module (223) receives the commands from the controller (100) to adjust the bevel orientation by rotating the needle unit (200) in the step (1120). When the first driving module (16) operates, the body (19) rotates about the first rotation axis (17), thereby rotating the needle unit (200) supported by the support arm (14).

In the embodiments illustrated in FIGS. 4 to 6, when the seventh driving module (223) operates, the rollers (214) rotate, thereby rotating the needle unit (200) to adjust the bevel orientation to the predetermined orientation.

In the step (1130), after the bevel orientation is adjusted to the predetermined orientation, the first driving module (16) or the seventh driving module (223) stops working and then the adjusted information of the bevel orientation is synchronized with the value recorded in the controller (100).

Figure 11:
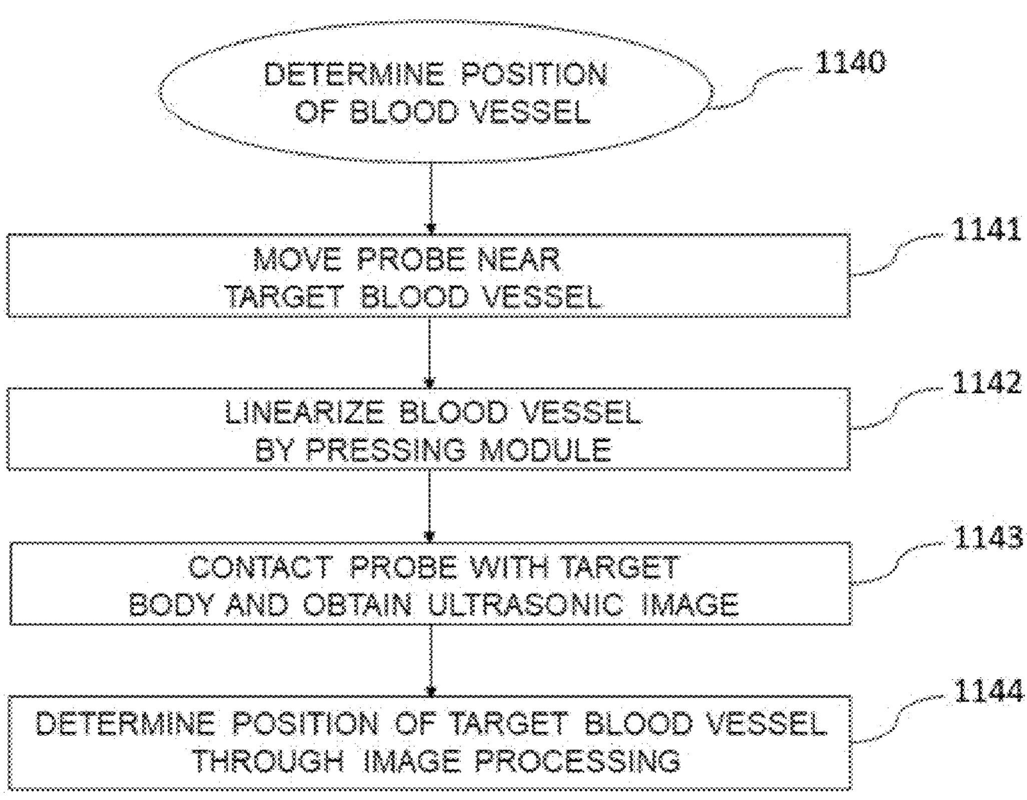
FIG. 11 is a flowchart of the method for determining a target of a body in the process illustrated in FIG. 10.

Subsequently, the location of the target body is determined in the step (1140). FIG. 11 shows the determination process if the target body is a superficial vein.

In the step (1141), the probe (41) moves to the position close to a blood vessel. Subsequently, in the step (1142), the probe unit (40) moves to linearize the blood vessel while the pressing module (48) presses the blood vessel. The pressing module (48) can be configured to move on the target body over a predetermined distance. Ultrasonic scanning and blood collection can be easily performed for the blood vessel which is linearized by the pressing module (48). The pressing force by the pressing module (48) can be optimized uniform force between 0 to 19.6 N (including boundary values).

In the step (1143), the probe (41) comes in contact with the target body and obtains ultrasonic image thereof after the linearization of the blood vessel is completed. The location of target blood vessel is determined through image processing to the obtained ultrasonic image in the step (1144).

Referring to FIGS. 12 to 15, the method of determining the location of a superficial vein is described in below.

In the step (1150), the needle unit (200) moves to the second position. If the adjustment unit for bevel orientation is disposed in the first position or near thereof, the needle unit (200) can be transferred to the second position from the first position by the movable arm (24) which is rotated by the second driving module (23) receiving the commands from the controller, in the state that the movable arm (24) supports the needle unit (200), the bevel orientation of which is adjusted. The transfer to the second position from the first position can also be achieved by other known kinematical mechanisms or variation thereof.

If the adjustment unit for bevel orientation is disposed in the second position or near thereof, the step (1150) can be unnecessary. In the embodiments, the bevel orientation is adjusted in the state the needle unit (200) is supported by the moving unit of needle (30) as illustrated in FIGS. 2 to 6.

If the adjustment unit for bevel orientation is disposed in the third position, the movable arm (24) moves to the third position from the first position; the bevel orientation is adjusted at the third position; and then the movable arm (24) moves to the second position from the third position.

The main body (31) is rotated to have an appropriate angle for body insertion by the third driving module (33) receiving the commands from the controller (100) in the state that the needle unit (200) is supported by the moving unit for needle (30) at the second position. Subsequently, the fourth driving module (34) moves the connecting member (35) in the lengthwise direction of the second main body (31) in accordance with the commands from the controller (100), thereby inserting the needle into the body. If the target body is a superficial vein, blood collection can be performed after the needle is inserted. The second main body (31) can be configured to move in at least one of the left and right directions in FIGS. 7 and 8 or any other direction.

Hereinafter, described is the method for determining the location to be inserted by a needle based on image processing of the image obtained by the ultrasonic probe (41). The description is for an example of a superficial vein. The method is disclosed by KR Patent No. 10-2246966 and is just for understanding of the present disclosure. It should be understood that the method described hereinafter does not limit the scope of the present disclosure.

Figure 12:
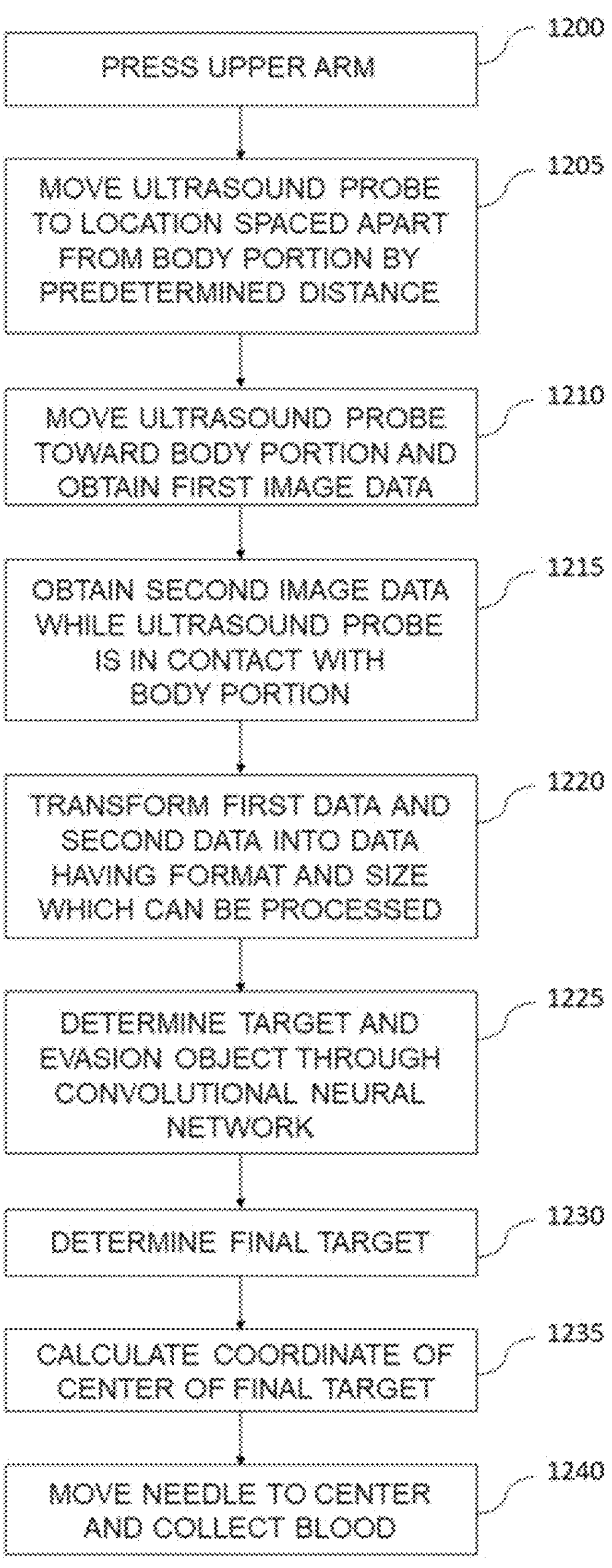
FIGS. 12 to 15 are the drawing for describing the method for determining a target of a body in detail.

FIG. 12 shows the process of the method for determining the location of the superficial vein through the ultrasonic probe.

In the step (1200), a person to be examined places an upper arm into the unit for pressing upper arm (not illustrated) and then the unit presses the upper arm. The unit can comprise an annular strap having a width of 1 to 5 cm. The strap can press the upper arm 3 to 12 cm above an elbow, preferably 6 to 8 cm above the elbow. The pressure applied to the upper arm can be 10 to 60 mmHg, preferably 20 to 30 mmHg. The following processes can be carried out even without pressing the upper arm.

Although it is illustrated in FIG. 12 that the upper arm is pressed before the ultrasound probe (41) moves, the upper arm can be pressed after the ultrasound probe (41) moves and starts to obtain image data. If the upper arm is pressed after the ultrasound probe starts to obtain the first image data, the first image data can include an image data obtained before the upper arm is pressed and an image data obtained after the upper arm is pressed.

In the step (1205), the ultrasound probe (41) moves to the position spaced apart from the body portion by a predetermined distance, for example 1 mm, after the upper arm is pressed. The ultrasound probe (41) can be moved to a median cubital vein, which is 0 to 8 cm, preferably 1 to 3 cm, from a cubital fossa toward a hand.

In the step (1210), a first image data is obtained while the ultrasound probe (41) moves toward the body portion. The first image data is obtained before the ultrasound probe (41) comes into contact with the body portion. The first image data can include an image data obtained before the upper arm is pressed and an image data obtained after the upper arm is pressed.

A second image data is obtained while the ultrasound probe (41) is in contact with the body portion and presses the body. According to the alternative aspect of the present disclosure, the body can be pressed by an alternative device.

The first and second image data can include the image data which is analyzed through Doppler effects among the soundwave signals of blood flow. According to another embodiment of the present disclosure, only one of the first image data and the second image data can be used.

In the step (1220), an image data processing module transforms the first image data and the second image data into the data having the format and size which can be processed by the program codes of the present disclosure. Alternatively, the image data can be processed without the transformation.

In the step (1225), the transformed image data is analyzed by a machine learning server by use of, for example, Convolution Neural Network; and then the pixels of the target and the evasion object are identified.

In this specification, the target can be a blood vessel such as a superficial vein or an artery; the evasion object can be an artery, a nerve, bone tissue, and the like. The target and the evasion object are differently defined according to the purpose of finding the target. An artery, a nerve, or bone tissue which is regarded as an evasion object when the purpose is finding a superficial vein, can be classified as a target for another purposes.

The target and the evasion object can be displayed by pixels or a bounding box. The bounding box can be generated by use of center value, boundary, and distance. The information which can define the shape of the target or the evasion object can be also stored. The information can be a center value, the information about the shape of the target or the evasion object, for example, circle/ellipse, rectangle, and the like. The information can also include a radius, distance between at least two points, a length of one side, and the like.

The present disclosure using Convolutional Neural Network learning (hereinafter referred to as "CNN learning") is described in the below.

For performing CNN learning, learning through data should be carried out in advance. The image data which is used in CNN learning can be pre-processed to increase its generality by use of data augmentation techniques, for example, random cropping, size transformation, horizontal flip of the first and second image data, and the like.

The machine learning server obtains the feature information of the target and the evasion object through CNN learning and stores the feature information.

The feature information can include at least one of the intensity of echogenicity of the components identified in the ultrasonic image data; the distribution pattern of the echogenic components; the information about the relative position of the distribution of the components; the height, weight, sex, and age, morbidity, and the information about the treatment to the person in the past and/or the present; the information obtained in the pressing process by the ultrasound probe and other devices; and real-time blood flow information analyzed through Doppler effects.

When the skin surface is pressed with an ultrasound probe or other devices, veins are directly decreased in size, or swell due to the pressed proximal portion to induce congestion, unlike arteries. The information obtained in the pressing process by the ultrasound probe and other devices can include the information about the state change of the vein and the like.

Doppler signal from arteries is strong since the arteries periodically beat and blood flow thereof is fast. Therefore, the real-time blood flow information is useful to detecting the target such as a superficial vein or an artery.

Training by CNN learning can be performed so as to display the pixels at the location of the target and the evasion object, based on the feature information.

The learning (training) can be a supervised learning, an unsupervised learning, or a semi-supervised learning.

In the supervised learning, the training can be performed by using the images having correct answers. If the target and the evasion object which are identified in the image by CNN learning is different from the correct answers, the learning can be performed so that the loss of the loss function reduces. The loss function can be BCEloss (Binary Cross Entropy loss), Cross entropy, and the like. Optimizer can be Adam Optimizer, RMSprop, Stochastic Gradient Descent and the like. Evaluation can be performed by Dice Coefficient Loss and the like.

After the target and/or the evasion object are identified through a machine learning, for example, CNN learning, the step (1230) is carried out for determining a final target based on the identified objects.

Figure 13:
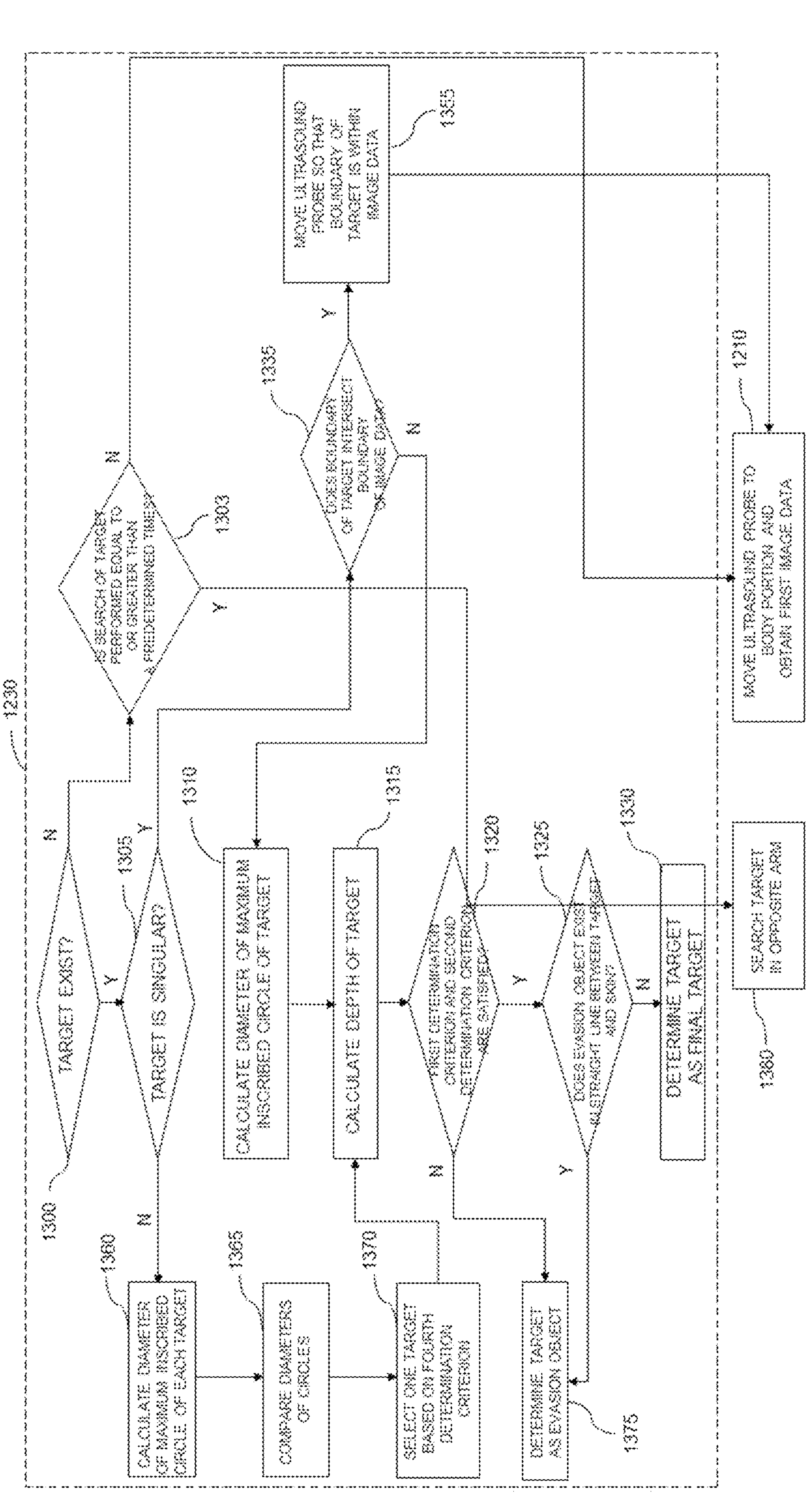
Figure 14:
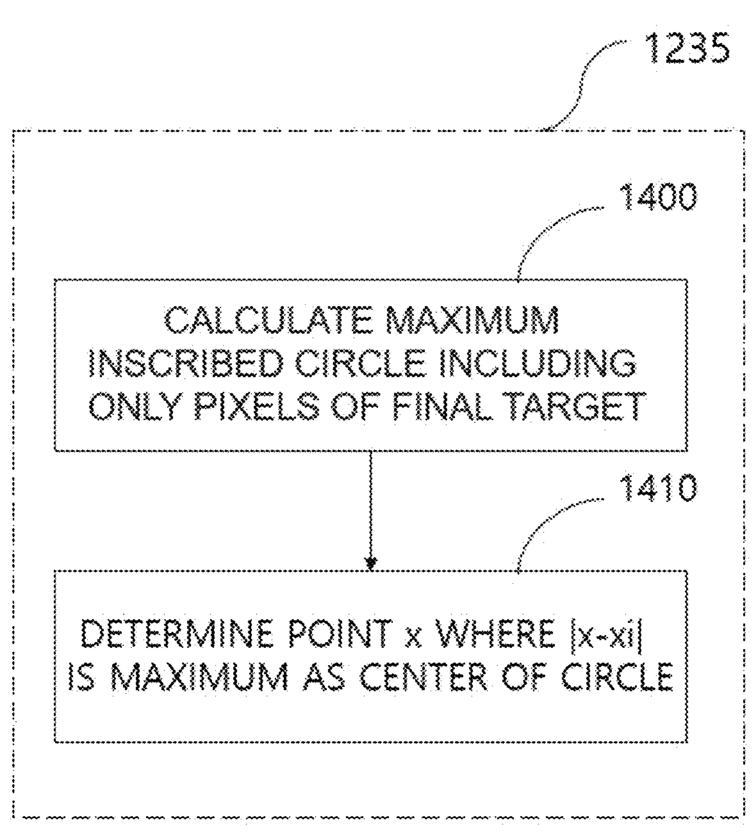

FIG. 13 shows the flowchart of the detailed processes included in the step (1230).

In the step (1300), it is determined whether the target which is to be sought is identified in the previous steps. If the target exists, the number of the target is counted in the step (1305).

If the number of the identified target is one, it is determined in the step (1335) whether the boundary of the target intersects the boundary of the image. If they do not intersect each other, the step (1310) is carried out. Otherwise, in the step (1355), the ultrasound probe (41) moves to other position, for example, in the center of the image, so that the coordinate value of the boundary of the target is within the inside of the image. Subsequently, the process returns to the step (1210) and then the steps following the step (1210) are carried out. The body of the person to be examined can move instead of moving the ultrasound probe (41).

In the step (1310), the diameter of the maximum inscribed circle, which is one of the size-based information of the target, is calculated. The maximum inscribed circle means the largest circle including only the pixels of the target. The size-based information of an object can be the maximum/minimum lengths of horizontal and vertical lines that can be drawn within the object, the maximum/minimum distances between the center of gravity of the object and the boundary of the object, the area of the object, and the like, further to the diameter of maximum inscribed circle.

In the step (1315), the depth of the target, which is one of the depth-based information is calculated. It is determined in the step (1320) whether the target satisfies a first and a second determination criteria. The depth-based information includes various information relating to depth.

If the target is a superficial vein, the first determination criterion is whether the diameter of maximum inscribed circle is greater than or equal to a predetermined value (a first value). For example, if a diameter of maximum inscribed circle of the identified target is less than 2 mm, the target can be classified as an evasion object in the step (1375). If the diameter of maximum inscribed circle is greater than or equal to the first value, it is determined that the first determination criterion is satisfied. The first value can be determined with reference to a device operation error range.

If the size-based information relates to a horizontal line and a vertical line which can be drawn in the object, the first determination criterion can be whether the maximum and/or minimum lengths of the horizontal/vertical lines is greater than or equal to a predetermined value. For example, if the minimum length of the horizontal line and the vertical line of the identified target is less than 2 mm, the target is classified as an evasion object. If the target satisfying the first determination criterion is not singular, the object having the largest value in sum, product, average and the like of the lengths can be determined to be a candidate of a final target in the step (1370).

If the size-based information is a maximum distance and a minimum distance between a center of gravity and a boundary line, the first determination criterion is whether the distance is greater than or equal to a predetermined value. For example, if the minimum distance between the center of gravity of the target and the boundary line of the target is less than 2 mm, the target can be classified as an evasion object. If the target satisfying the first determination criterion is not singular, the target having the largest value in sum, product, average and the like of the distances can be determined to be a candidate of a final target in the step (1370).

If the size-based information is an area of an object, the first determination criterion is whether the area is greater than or equal to a predetermined value. For example, if the area of the target is less than 10 $mm^2$, the target can be classified as an evasion object. If the target satisfying the first determination criterion is not singular, the object having the largest area can be determined as a candidate of a final target in the step (1370).

The second determination criterion is whether the depth of an object is less than or equal to a predetermined value (second value), for example, 1 cm. If the depth of the target is larger than the second value, the target can be classified as an evasion object in the step (1375). This is to exclude a deep vein since the hemostasis of a deep vein is more difficult than that of a superficial vein as well as to exclude an artery which is an evasion object. Further, if the depth of the target is greater than the second value, a needle can make a deep wound while penetrating the body and there may be an important anatomical structure or nerves in the penetrating path. These are why the second determination criterion is necessary. If the depth of an object is less than or equal to the second value, it is determined that the second determination criterion is satisfied.

If the first and second determination criteria are satisfied, it is determined in the step (1325) whether another object is present in the straight path between the candidate and a skin surface. This is referred to as a third determination criterion. Another object which is present in the path may be a nerve that is an evasion object.

If the determination result is "NO" in the step (1325), the candidate is determined in the step (1330) as a final target.

Alternatively, the target which satisfies at least one of the first, second and third determination criteria can be determined as a final target.

The embodiments where a plurality of targets are identified in the step (1225) will be described in the below.

If a plurality of targets are identified, the size of the maximum inscribed circle of each target is calculated in the step (1360). In the step (1365), the size of the maximum inscribed circle of each target is compared to one another, and then a candidate of a final target is determined according to the fourth determination criterion in the step (1370). The other size-based information can be calculated and compared one another as described in the above in the alternative embodiments of the present disclosure.

The fourth determination criterion is as follows. In principle, the target having the largest size of the maximum inscribed circle thereof is selected as the candidate of the final target. However, if the difference between the largest size and the second largest size is within a predetermined value (a third value), for example, 10%, the target which is closer to the contact surface of the ultrasound probe, for example, the target which is closest to the center of the contact surface, can be selected as the candidate of the final target.

Even in the embodiments where the first information is the other size-based information, the fourth determination criterion can be applied as described in the above. That is, if the difference of compared size is within a predetermined value, a target which is closer to the contact surface of the ultrasound probe, for example, the target which is closest to the center of the contact surface, can be selected as the candidate of a final target.

The step (1315) and the steps following the step (315) are carried out after the candidate of the final target is selected in the step (1370), and then the candidate is determined to be the final target or an evasion object.

If it is determined in the step (1300) that a target does not exist, it is determined in the step (1303) whether the search of target has been performed greater than or equal to a predetermined number of times. If it is determined that the search has been performed greater than or equal to a predetermined number of times, for example, 2 or 3 times, the search for a target is carried out for an opposite arm in the step (1380). If it is determined that the search has been performed less than the predetermined number of times, the ultrasound probe (41) moves to a position which is different from that of the previous search and then obtains a first image data in the step (1210).

After the final target is determined according to the aforementioned steps, the coordinate value of the center of the final target is calculated in the step (1235). The needle is inserted to the center of the final target.

The center of the final target is defined by a point (x) which has the maximum distance from any point ($x_i$) inside the maximum inscribed circle including only the pixels of the final target.

If the straight line between the center and the skin surface crosses the surface of blood vessels greater than or equal to a predetermined number of times, for example, two times, the candidate of the final target can be excluded from the final target.

According to the optional embodiments of the present disclosure, a circle having a predetermined diameter, for example, 1 mm, is drawn for all pixels inside the final target; and then if a predetermined ratio of pixels within the circle, for example, 30 to 95%, preferably 50 to 70% are inside the final target, it is determined that the pixel is included in the final target. Otherwise, the pixel is excluded from the final target.

Figure 15:
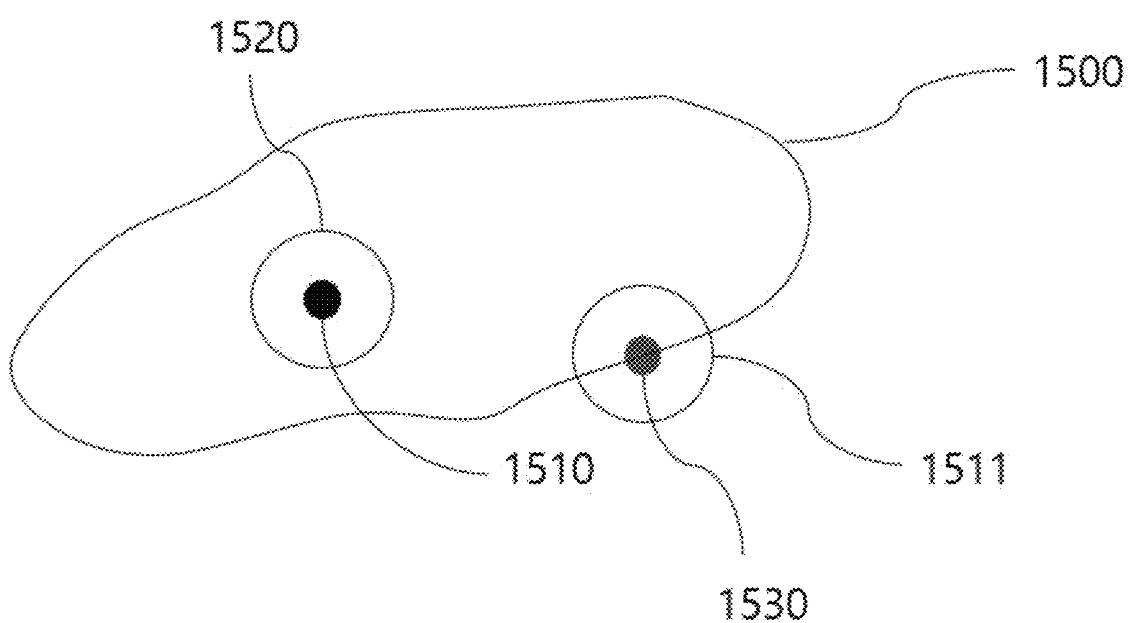

As illustrated in FIG. 15, because all the pixels in the circle (1520) are inside the final target, the pixel (1510) is determined to be a pixel of the final target. Because a predetermined portion of the pixels of the circle (1511) are not inside the final target, the corresponding pixel (1530) is excluded from the final target.

These processes are for softening the boundary of the final target and excluding the possibilities that a mis-classified pixel is present in the final target. However, the processes are optional, not essential in the present disclosure.

Although the present disclosure has been described with reference to accompanying drawings, the scope of the present disclosure is determined by the claims described below and should not be interpreted as being restricted by the embodiments and/or drawings described above. It should be clearly understood that improvements, changes and modifications of the present disclosure disclosed in the claims and apparent to those skilled in the art also fall within the scope of the present disclosure. Accordingly, this description is to be taken only by way of example and not to otherwise limit the scope of the embodiments herein.

What is claimed is:

1. A body-insertion device comprising:

an adjustment unit for adjusting bevel orientation of a needle of a needle unit;

an ultrasound probe unit configured to acquire an image of a body part, analyze the acquired image based on a trained neural network model to identify a target and avoidance objects in the body part, and determine a final target position based on at least one of first information related to a size of the target, second information related to a depth of the target, or third information related to whether an avoidance object exists on a straight path between the target and a skin surface of the body part; and a moving unit for the needle unit, wherein the adjustment unit comprises, a support arm comprising a pair of arms which are provided parallel to each other for supporting the needle unit, a hydraulic module for driving the support arm, a driving module for rotating the support arm, and a detector for detecting the bevel orientation of the needle of the needle unit, wherein the pair of arms of the support arm is configured to move away from each other by the hydraulic module and support the needle unit by applying an outward force to inner walls of the needle unit, wherein the driving module is configured to adjust the bevel orientation of the needle of the needle unit by rotating the support arm based on the detected the bevel orientation of the needle of the needle unit by the detector, wherein the ultrasound probe unit is further configured to determine whether a boundary of the target overlaps with a boundary of the image data, and when it is determined that the boundary of the target overlaps with the boundary of the image data, move so that a coordinate of the boundary surface is located inside the image and re-acquire the image of the body part, and wherein the moving unit is configured to support the needle unit with the bevel orientation of the needle being adjusted, adjust the needle unit to the orientation which is appropriate for body-insertion, and move the needle unit for body-insertion.

2. The device according to claim 1, further comprising a transfer unit for moving the needle unit to a second position from a first position.

3. The device according to claim 2, wherein the transfer unit comprises a movable arm which supports the needle unit, the movable arm moving between the first position and the second position.

4. The device according to claim 2, wherein the adjustment unit is provided in or close to at least one of the first position or the second position.

5. A computer-implemented method for controlling the device of claim 2, the method comprising:

a first step of, by the adjustment unit, adjusting the bevel orientation of the needle;

a second step of, by the transfer unit, moving the needle unit to the second position from the first position;

a third step of, by the moving unit, receiving the needle unit at the second position and supporting the needle unit;

a fourth step of, by the moving unit, adjusting the needle unit into the appropriate orientation for body-insertion; and a fifth step of, by the moving unit, moving the needle unit for body-insertion.

6. The device according to claim 1, wherein the adjustment unit comprises:

at least one roller which is configured to be in contact with the needle unit; and a seventh driving module which rotates the at least one roller, thereby rotating the needle unit.

7. The device according to claim 6, wherein the adjustment unit further comprises a movement prohibitor which prevents the needle unit from moving in the direction other than the rotation direction caused by the roller.

8. The device according to claim 6, wherein the at least one roller comprises a tooth portion which is in contact with an outer periphery of the needle unit or meshes with a tooth portion of the needle unit.

9. The device according to claim 1, wherein the ultrasound probe unit comprises a probe, a probe holder, and a pressing module for pressing the target body.

10. The device according to claim 9, wherein the ultrasound probe unit further comprises an elastic member for connecting the probe holder and the pressing module.

11. A computer-implemented method for controlling the device of claim 9, the method comprising:

a first step of, by the moving unit, supporting the needle unit;

a second step of, by the adjustment unit, adjusting the bevel orientation of the needle;

a third step of moving the pressing module on the target body while pressing a body;

a fourth step of, by the moving unit, adjusting the orientation of the needle unit into the appropriate orientation for body-insertion; and a fifth step of, by the moving unit, moving the needle unit for body-insertion.

12. The method according to claim 11, wherein the pressing module linearly moves on the body.

13. The method according to claim 11, wherein the pressing module moves on the body over a predetermined distance.

14. A computer-implemented method for controlling the device of claim 9, the method comprising:

a first step of, by the adjustment unit, adjusting the bevel orientation of the needle;

a second step of, by the transfer unit, moving the needle unit to the second position from the first position;

a third step of, by the moving unit, receiving the needle unit at the second position and supporting the needle unit;

a fourth step of moving the pressing module on the target body while pressing a body; and a fifth step of, by the moving unit, moving the needle unit for body-insertion.

15. A computer-implemented method for controlling the device of claim 1, the method comprising:

a first step of supporting, by the moving unit, the needle unit;

a second step of, by the adjustment unit, adjusting the bevel orientation of the needle;

a third step of, by the moving unit, adjusting the orientation of the needle unit into the appropriate orientation for body-insertion; and a fourth step of, by the moving unit, performing body-insertion.

16. The device according to claim 1, wherein the driving module is a rotation driving module or a linear driving module.

* * * * *